(12) United States Patent
Alain

(10) Patent No.: US 8,012,183 B2
(45) Date of Patent: Sep. 6, 2011

(54) VERTEBRAL ANCHORING DEVICE

(75) Inventor: Tornier Alain, Saint-Ismier (FR)

(73) Assignee: Clariance, Dainville (FR)

(*) Notice: Subject to any disclaimer, the term of this patent is extended or adjusted under 35 U.S.C. 154(b) by 470 days.

(21) Appl. No.: 12/211,837

(22) Filed: Sep. 17, 2008

(65) Prior Publication Data
US 2009/0076552 A1 Mar. 19, 2009

Related U.S. Application Data

(60) Provisional application No. 60/974,085, filed on Sep. 21, 2007.

(30) Foreign Application Priority Data

Sep. 17, 2007 (FR) ...................................... 07 06501

(51) Int. Cl.
A61B 17/70 (2006.01)
(52) U.S. Cl. ...................................................... 606/264
(58) Field of Classification Search .......... 606/246–279, 606/301
See application file for complete search history.

(56) References Cited

U.S. PATENT DOCUMENTS

| 7,722,651 B2 * | 5/2010 | Kwak et al. .................... 606/265 |
| 7,749,258 B2 * | 7/2010 | Biedermann et al. ......... 606/308 |
| 7,785,353 B2 * | 8/2010 | Sybert ............................ 606/272 |
| 7,850,718 B2 * | 12/2010 | Bette et al. ..................... 606/267 |
| 2005/0192571 A1 | 9/2005 | Abdelgany |
| 2007/0118123 A1 | 5/2007 | Strausbaugh et al. |
| 2008/0306552 A1 * | 12/2008 | Winslow et al. ............... 606/301 |

FOREIGN PATENT DOCUMENTS

| EP | 1570796 | 9/2005 |
| WO | 2007047711 | 4/2007 |

OTHER PUBLICATIONS

French search report in corresponding FR0706501.

* cited by examiner

Primary Examiner — Eduardo C. Robert
Assistant Examiner — Stuart S Bray
(74) Attorney, Agent, or Firm — Young & Thompson

(57) ABSTRACT

A vertebral anchoring device includes connectors (2) linked to one another by connecting rods (3) and fixed on bone-anchoring screws (5) implanted in the vertebrae (4) of a vertebral column, each connector (2) being composed of a connection element (6) that includes receiving and fixing members to permit immobilization of the connecting rod (3) in translation and in rotation. Each connection element (6) includes, opposite the members for receiving and fixing the connecting rod (3), a seat (12) that cooperates with a connecting device (17) permitting assembly of the anchoring screw (5). The connecting device (17), before immobilization of the connecting rod (3) in the connection element (6), permits lateral and independent tilting movements of the connection element (6) and of the anchoring screw (5) relative to each other, and rotation of the anchoring screw (5) for fixing it in the body of the vertebra (4).

11 Claims, 10 Drawing Sheets

VERTEBRAL ANCHORING DEVICE

BACKGROUND OF THE INVENTION

The present invention relates to a vertebral anchoring device comprising bone-anchoring connectors that are fixed, by way of anchoring screws, to the various osseous bodies or vertebrae of a vertebral column.

DESCRIPTION OF THE RELATED ART

The U.S. Pat. No. 2,346,346 has disclosed an external bone-anchoring device comprising connectors that are linked to one another by a connecting rod, while each connector is fixed to a support or to the osseous body by way of an anchoring screw with a spherical head.

Each connector is composed of a cylindrical sleeve having, at each end, a bore of different diameter which, respectively, allows the screw to be introduced through said sleeve and allows the spherical head to be held inside the latter.

Each connector comprises a blocking device that simultaneously permits immobilization of the connecting rod inside the sleeve and fixation thereof about the spherical head of the screw.

It will be noted that, in order to fit this anchoring device in place, it is essential to join the anchoring screw and the connector together before fixing said screw either to a support or to the corresponding bone.

In this case, the spherical head of the screw is housed inside the connector, making it difficult to use same for anchoring it to the support or bone.

The international patent WO 2004/047657 discloses a vertebral anchoring device comprising a connector, a connecting rod, and a polyaxial anchoring screw. The polyaxial screw comprises a spherical head and a threaded body whose external diameter d at the summit of the teeth of the thread is greater than the external diameter a of the spherical head.

Each connector of the vertebral anchoring device is composed of a connection element with vertical branches delimiting a U-shaped opening, and of a locking clip equipped with a press-screw for blocking the connecting rod in the bottom of the U.

The connection element of each connector is provided centrally with a vertical bore that is able to receive, opposite the opening, a blocking device formed by a ring and by a threaded bushing, for placing and positioning said connector on the spherical head of the anchoring screw.

SUMMARY OF THE PRESENT INVENTION

The object of the present invention is to make available a vertebral anchoring device in which each connector comprises connecting means that permit, on the one hand, angular adjustment of said connector about the anchoring screw and, on the other hand, rotation of the anchoring screw for fixing it in the body of the vertebra.

The vertebral anchoring device according to the present invention comprises connectors that are linked to one another by connecting rods and are fixed on bone-anchoring screws implanted in the vertebrae of a vertebral column, each connector being composed of a connection element that comprises receiving and fixing means to permit immobilization of the connecting rod in translation and in rotation, each connection element comprising, opposite the means for receiving and fixing the connecting rod, a seat that cooperates with a connecting device permitting assembly of the anchoring screw, which connecting device, before immobilization of the connecting rod in the connection element, permits, on the one hand, lateral and independent tilting movements of the connection element and of the anchoring screw relative to each other and, on the other hand, rotation of the anchoring screw for fixing it in the body of the vertebra.

The vertebral anchoring device according to the present invention comprises a connection element composed of a bushing that cooperates with the seat of the connection element and has first means of rotation which are formed respectively in the seat and the bushing and allow the latter to tilt laterally about rotation pins, and second means of rotation which are formed respectively in the bushing and the head of the anchoring screw and allow the latter to tilt laterally about another rotation pin.

The vertebral anchoring device according to the present invention comprises a bushing which has at its center, and extending in a vertical direction, a through-bore designed to receive the head of the anchoring screw.

The vertebral anchoring device according to the present invention comprises a bushing which has, extending in a first horizontal direction, a first bore that opens into the inner bore and permits placement of the rotation pins, such that the latter open into the bores formed in the seat of the connection element, so as to permit the first lateral tilting movement.

The vertebral anchoring device according to the present invention comprises a bushing which has, extending in a second horizontal direction perpendicular to that of the first bore, a second bore that also opens into the inner bore and permits placement of a fixation pin that passes through a bore formed in the head of the anchoring screw, so as to permit the second lateral tilting movement.

The vertebral anchoring device according to the present invention comprises a bushing with an upper peripheral edge which has, on the one hand, a hump arranged above each first through-bore and, on the other hand, ribs arranged above each second bore and inside the inner bore.

The vertebral anchoring device according to the present invention comprises a bushing joined to a ring which, at its center, has a hole extending in a vertical direction, and, on its outer circumference, has recesses cooperating with the ribs of said bushing.

The vertebral anchoring device according to the present invention comprises a connection element with means for receiving and fixing the connecting rod, said means being composed of upper vertical branches that delimit a U-shaped opening for receiving said connecting rod, said upper vertical branches comprising, above the bottom of the opening, a threaded section that allows a press-screw to be tightened in order to block the connecting rod in translation and in rotation.

The vertebral anchoring device according to the present invention has a connection element comprising, below the threaded section and at the base of each vertical branch, an opening that opens into the inside of said connection element, in the area of the communication between the bottom of the opening and the seat, in a horizontal direction perpendicular to that of the connecting rod.

In the vertebral anchoring device according to the present invention, each of the openings of the connection element arranged opposite each other has an oblong vertical profile.

In the vertebral anchoring device according to the present invention, the through-bores of the connection element are arranged in a direction that is horizontal and perpendicular to that of the oblong openings.

The vertebral anchoring device according to the invention comprises other features that are essential to the invention and that are described and protected in the secondary claims dependent directly or indirectly on the main claim.

BRIEF DESCRIPTION OF THE DRAWING FIGURES

The attached drawings, given by way of example, will permit a better understanding of the invention, of its features, and of the advantages it is likely to afford.

DESCRIPTION OF THE PREFERRED EMBODIMENTS

Figure 1:
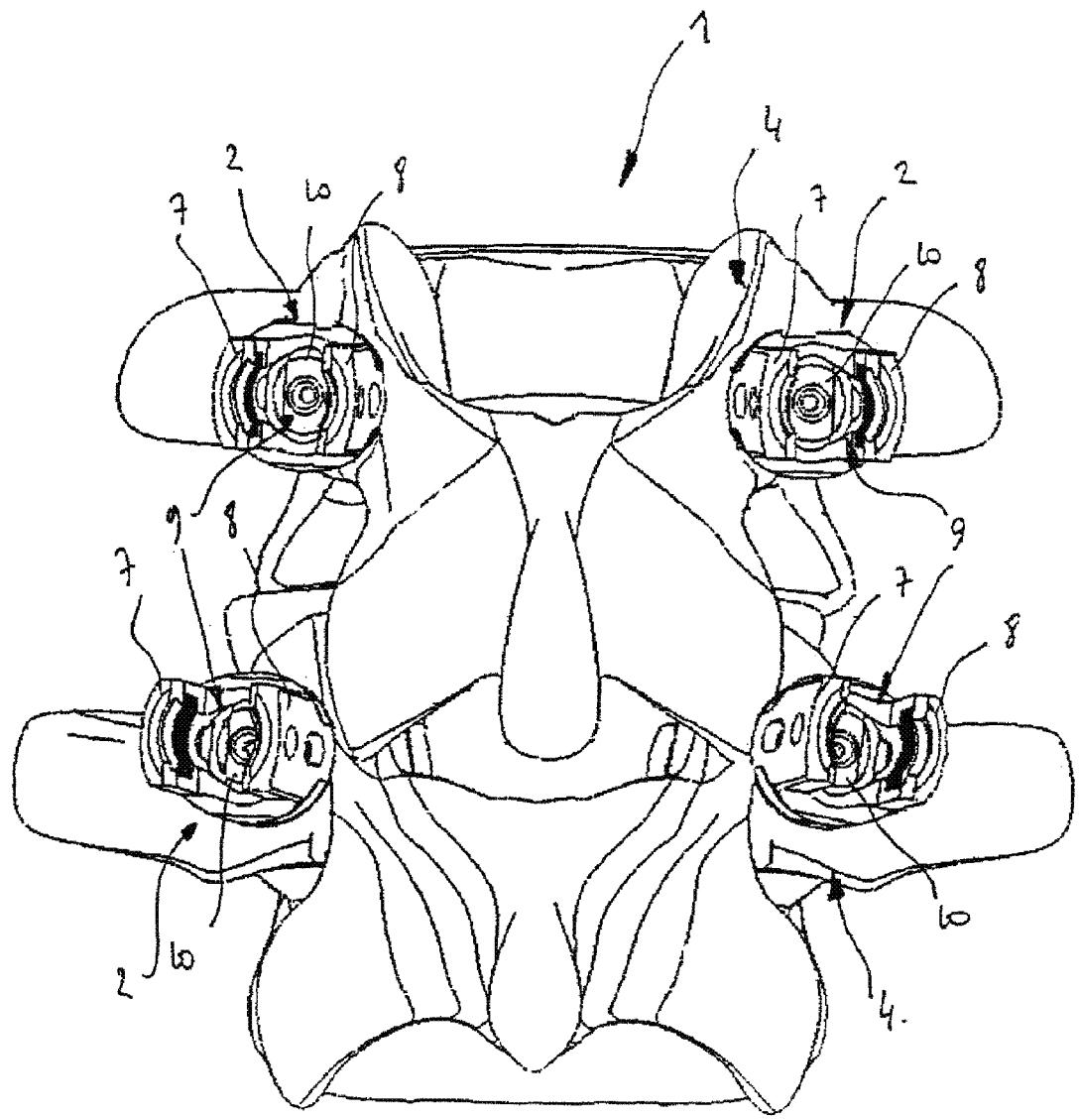
FIG. 1 is a plan view showing vertebral bodies of a vertebral column in which bone-anchoring connectors according to the present invention are fixed.
Figure 2:
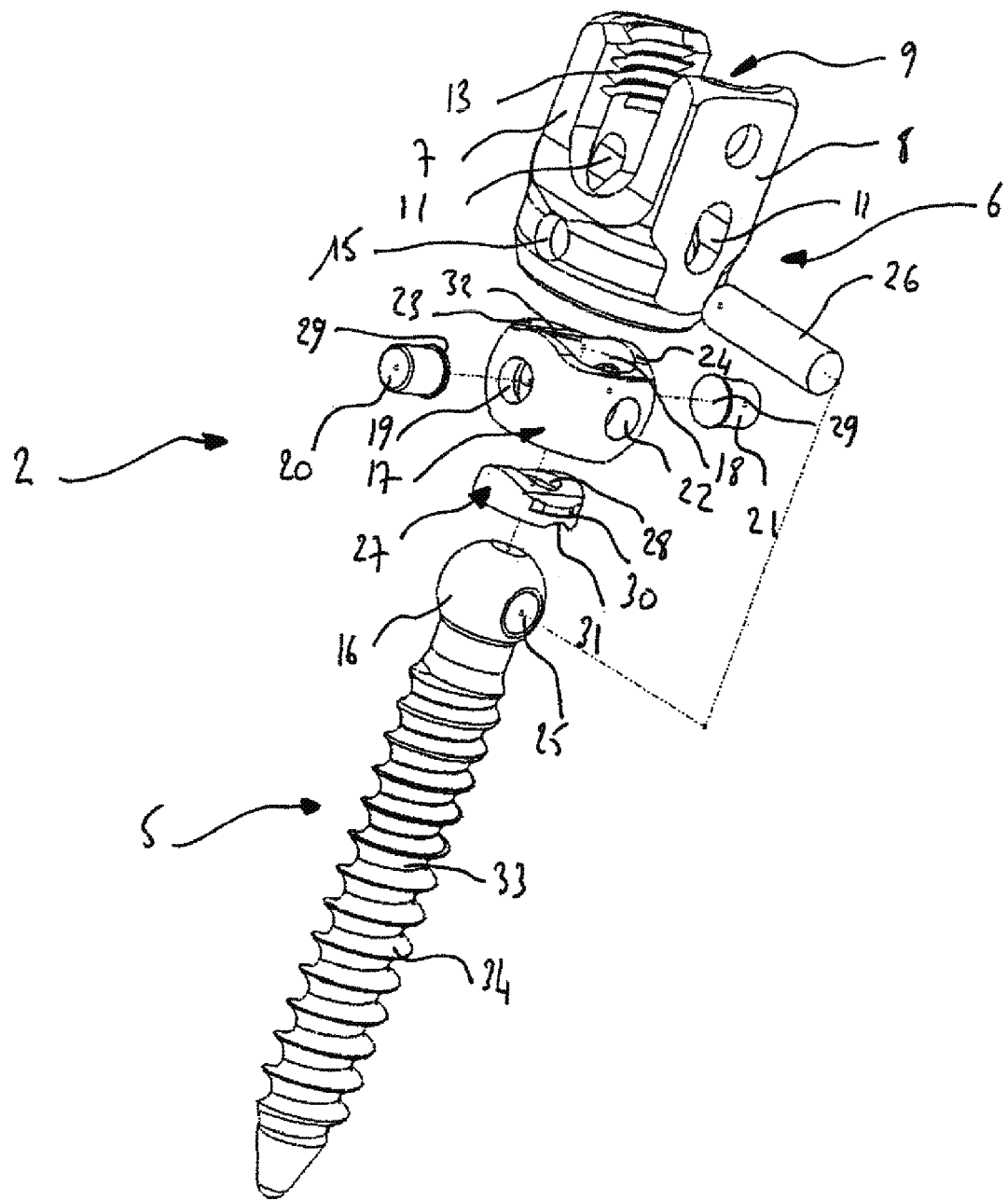
FIG. 2 is an exploded perspective view illustrating the bone-anchoring connector and its anchoring screw according to the present invention.
Figure 3:
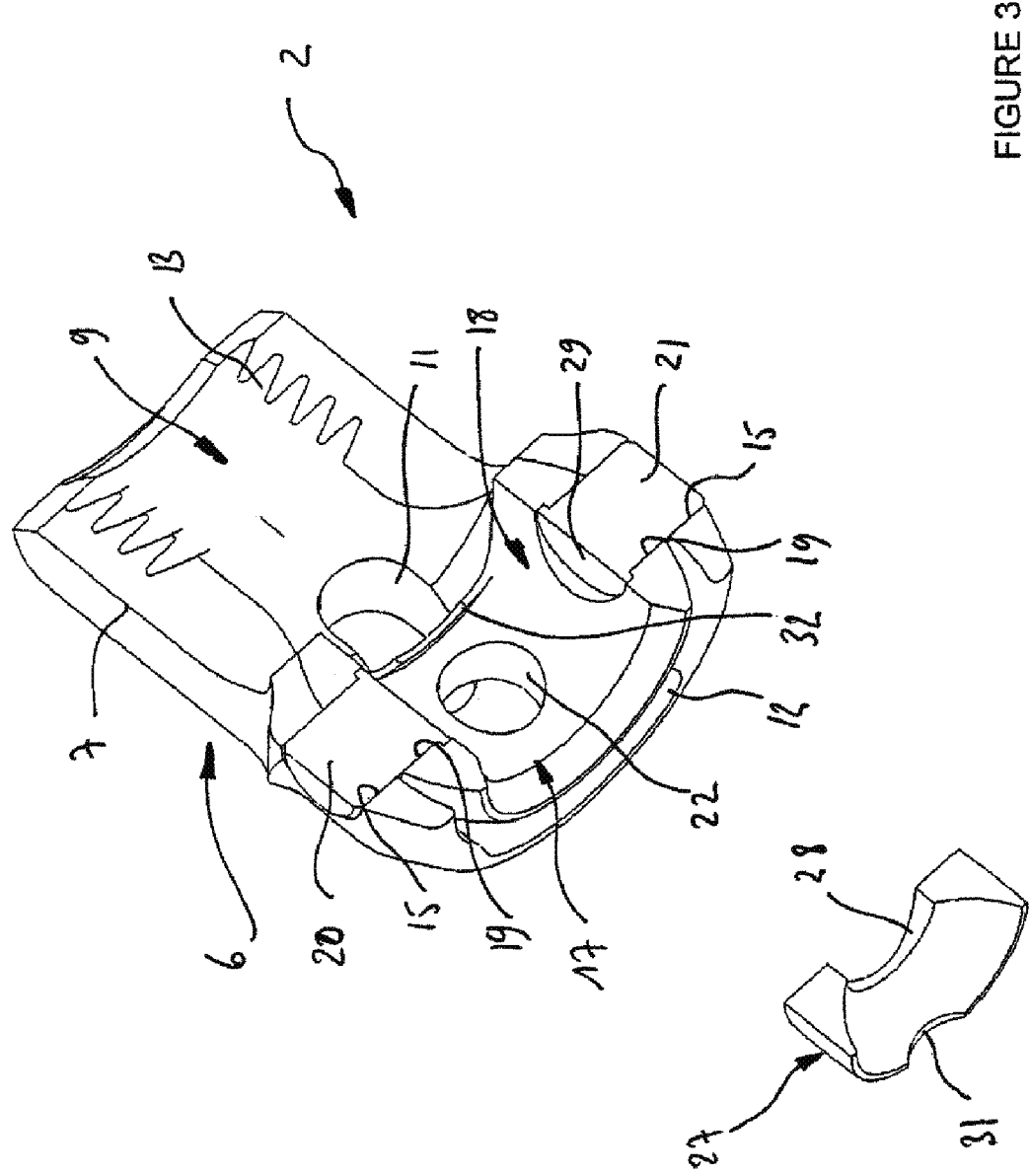
FIGS. 3 to 7 are views showing the assembling of the bone-anchoring connector with its bone-anchoring screw according to the present invention.

A vertebral anchoring device 1, shown in FIGS. 1 to 4, comprises connectors 2 that are linked to one another by connecting rods 3, while each connector 2 is fixed by an anchoring screw 5 in each vertebra 4 of a segment of the spine that is to be corrected.

Each connector 2 is composed of a connection element 6 that comprises upper vertical branches 7, 8 delimiting a U-shaped opening 9, the bottom 10 of which opening 9 communicates, opposite the opening 9, with a seat 12 which opens to the outside and whose inner profile can be in the shape of a portion of a sphere.

Figure 8:
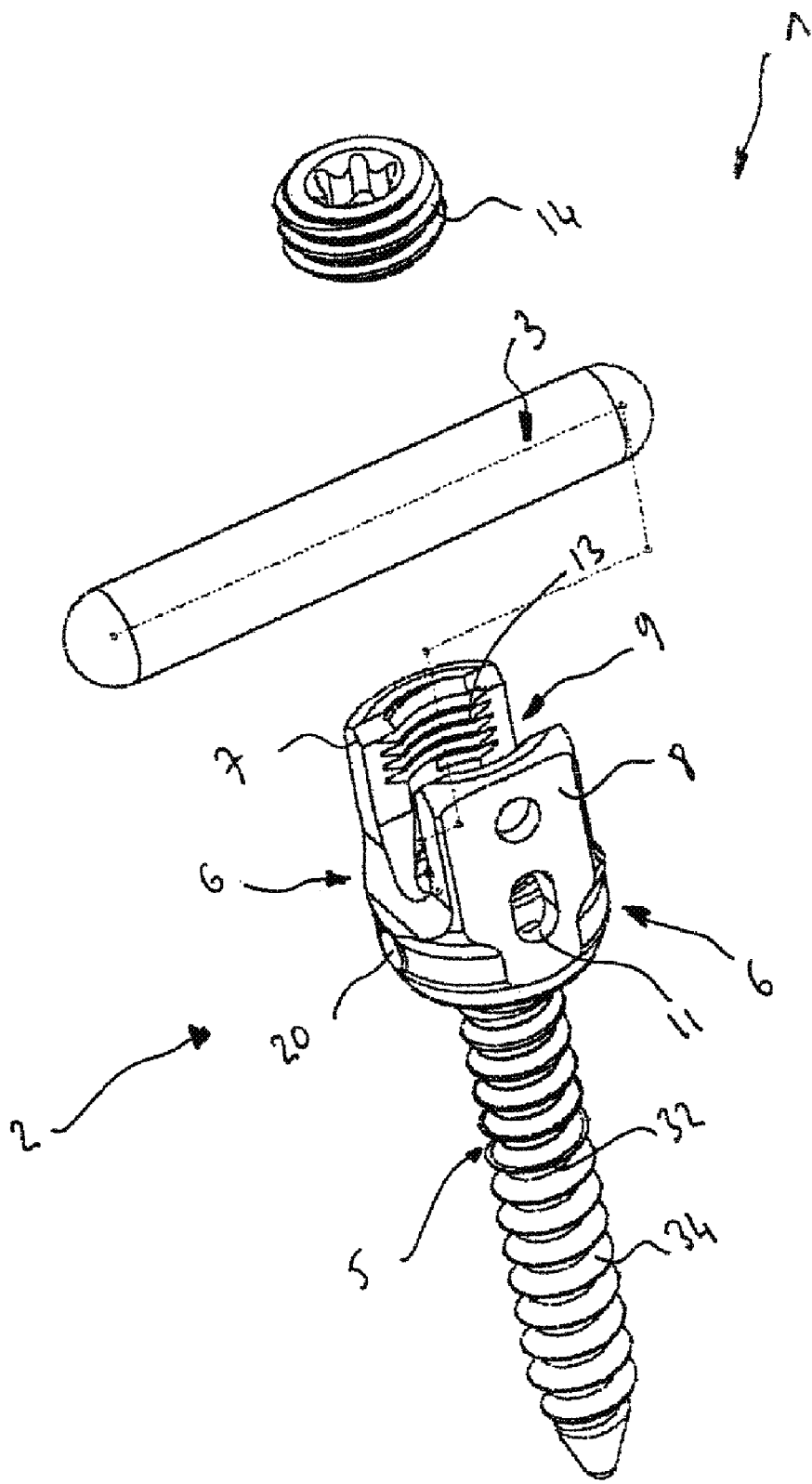
FIGS. 8 and 10 are views showing the bone-anchoring connector receiving a connecting rod according to the present invention.

The inner part of the upper vertical branches 7, 8 of the connection element 6 comprises, above the bottom 10 of the opening 9, a threaded section 13 that allows a press-screw 14 to be tightened in order to block a connecting rod 3 in translation and in rotation in the bottom of the U of each connector 2 (FIG. 8).

The connection element 6 comprises, below the threaded section 13 and at the base of each vertical branch 7, 8, an opening 11 that opens into the inside of said connection element, in the area of the communication between the bottom 10 of the opening 9 and the seat 12, in a horizontal direction perpendicular to that of the connecting rod 3.

Each of the openings 11 arranged opposite each other has an oblong vertical profile of sufficient height to permit introduction of a rotation pin 26 during assembly of the connector 2.

The seat 12 of the connection element 6 comprises coaxial through-bores 15 that extend in a horizontal direction perpendicular to that of the oblong openings 11.

Each connector 2 comprises a bushing 17 with an outer profile that complements the inner profile of the seat 12 formed in the lower part of the connection element 6.

The bushing 17 is provided centrally, and along a vertical axis, with an inner bore 18 in which the anchoring screw 5, and more particularly the head 16 thereof, is housed and immobilized.

The bushing 17 has, in a first horizontal direction, a first bore 19 that opens into the inner bore 18, and, in a second horizontal direction perpendicular to the first, a second bore 22 that also opens out into the inner bore 18.

The bushing 17 comprises an upper peripheral edge 23 which has a hump 24 arranged above each first through-bore 19.

The bushing 17 comprises ribs 32 arranged above the second bores 22 and in the area of the upper edge 23 of and inside the bore 18.

Each connector 2 comprises a ring 27 which, at its center, has a hole 28 extending in a vertical direction.

The ring 27 comprises, on its outer circumference, recesses 30 below which there are indents 31 shaped as a portion of a cylinder.

The connection elements 6 of each connector 2 are fixed in each vertebra 4 by the anchoring screw 5. Each anchoring screw 5 comprises a head 16, which is continued by a cylindrical body 33 with a thread 34 on its outer circumference.

The head 16 of the anchoring screw 5 has an outer profile that may or may not be of a shape complementing that of the inner bore 18 of the bushing 17.

The head 16 of the anchoring screw 5 has a through-bore 25 designed to cooperate with the fixation pin 26 when placed inside the connection element 6 of each connector 2.

Thus the fitting of each connector 2 of the vertebral anchoring device 1 around the anchoring screw 5 will be easily understood from the above description.

Figure 4:
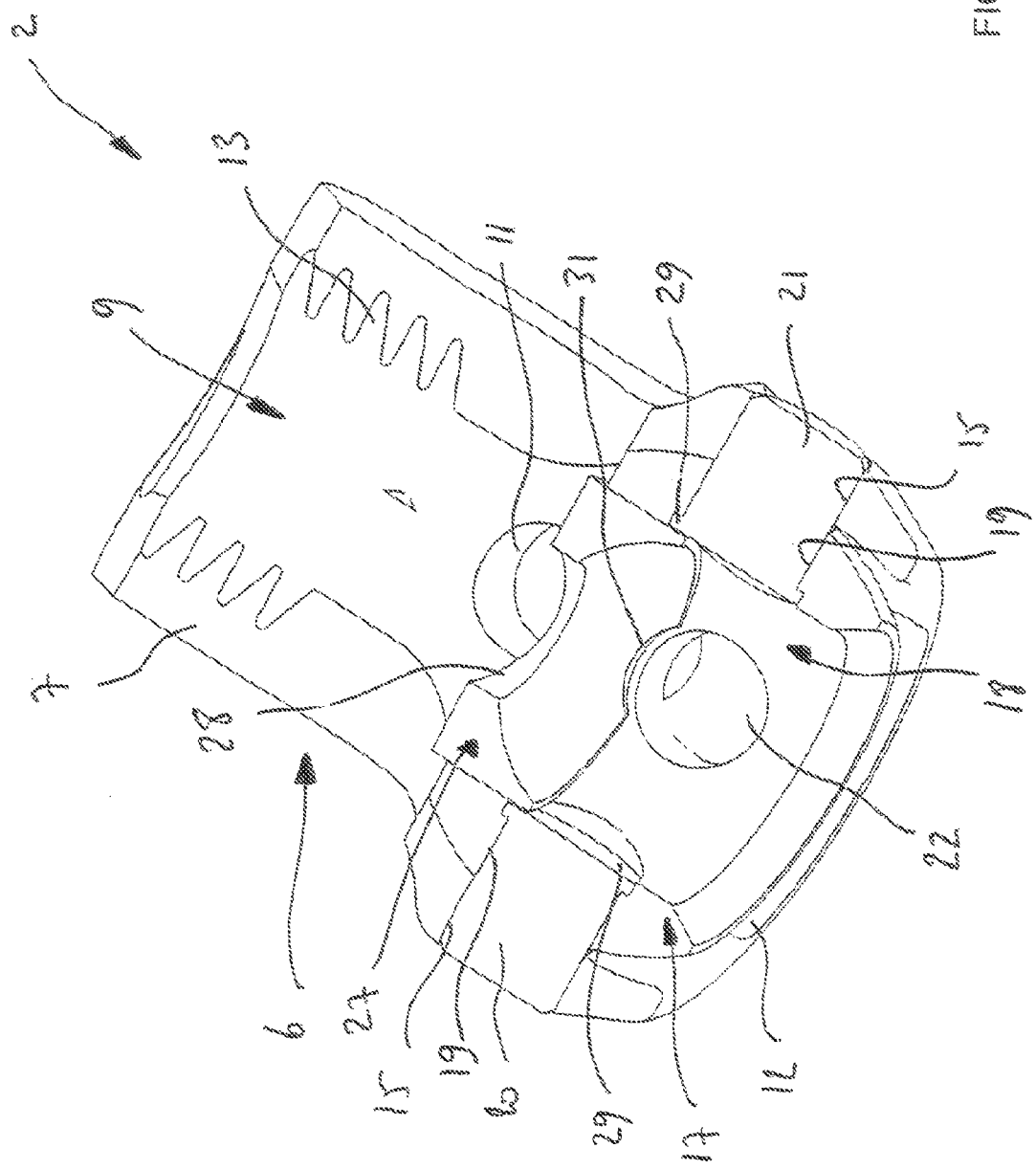

First, the bushing 17 is introduced into the seat 12 of the connection element 6 in such a way that each first bore 19 is arranged in line with those 15 of said seat (FIG. 4).

The bushing 17 is immobilized inside the seat 12 by way of two rotation pins 20, 21 which are each introduced through the inside of the bore 18 of the bushing 17 so as to cooperate with the bores 19 and 15 provided for this purpose.

The rotation pins 20, 21 comprise a head 29 whose external diameter is greater than the internal diameter of the bores 19, 15, so as to avoid any translation of these pins.

The introduction of the rotation pins 20, 21 into the horizontal bores 19, 15 makes it possible, on the one hand, to retain the bushing 17 in the seat 12 of the connection element 6 and, on the other hand, to permit a freedom of movement, that is to say a rotation or an angular clearance about said horizontal pins 20, 21 between said bushing 17 and the connection element 6 (FIG. 4).

Second, the ring 27 is introduced into and immobilized inside the inner bore 18 of the bushing 17 by means of the recesses 30, which cooperate with the ribs 32 provided in the area of the upper edge 23 (FIG. 4).

The ring 27 is immobilized inside the bushing 17, ensuring, on the one hand, that the indents 31 shaped as a portion of a cylinder are arranged above the horizontal bores 22 formed in said bushing 17, and, on the other hand, that the outer circumference of said ring opposite said indents bears against the rotation pins 20, 21 in order to prevent these from moving inside the bores 19 and 15.

The ring 27 is fixed in the bushing 17 in order to continue the latter above its upper edge 23, such that said ring 27 takes up a position at the bottom 10 of the opening 9 of the connection element 6.

Figure 5:
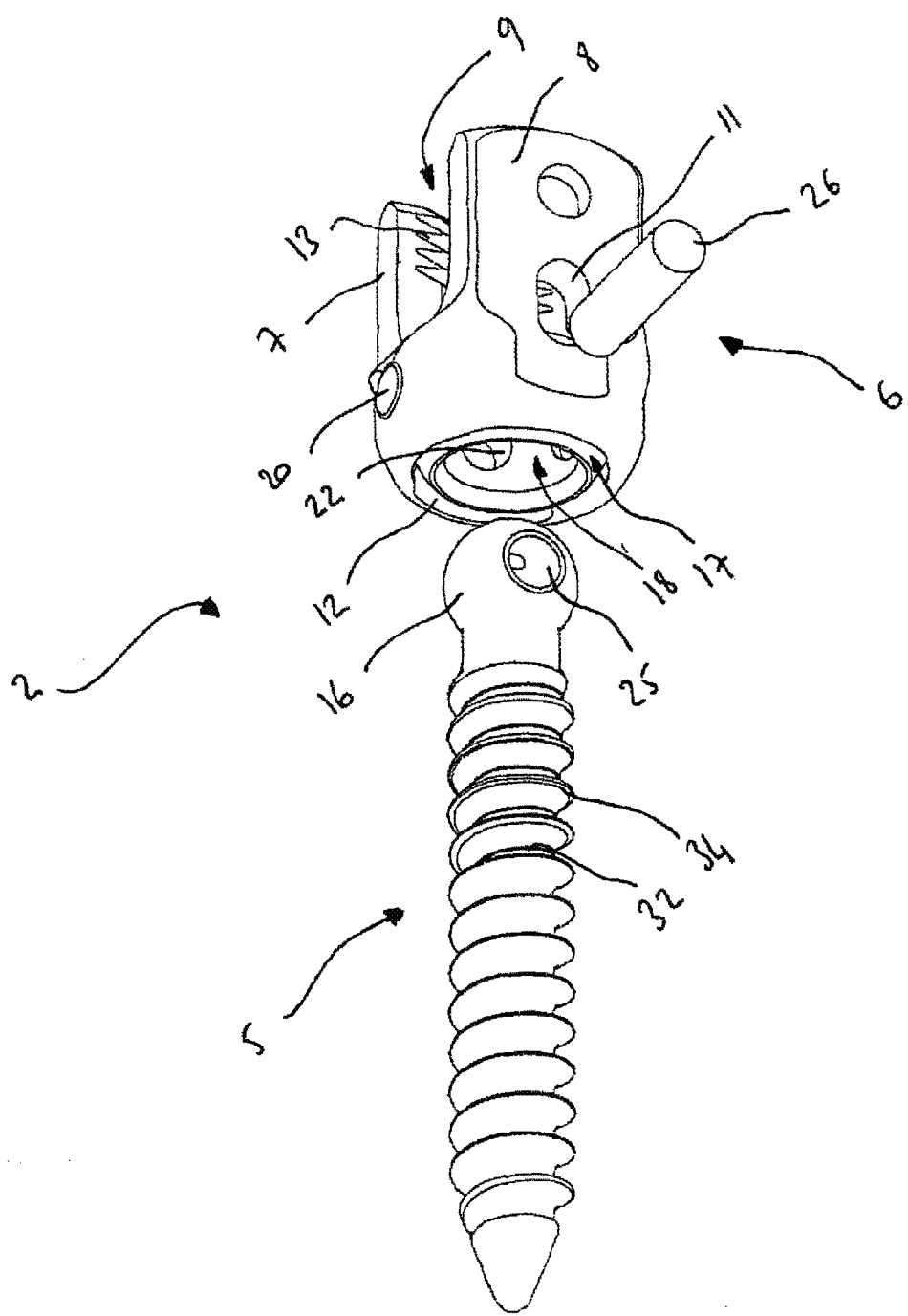

Third, the head 16 of the anchoring screw 5 is introduced into the bore 18 of the bushing 17, which is retained inside the seat 12 of the connection element 6. For this purpose, the bushing 17 must be positioned in such a way that the lower opening of the bore 18 is in alignment with that of the seat 12 of the connection element 6 (FIGS. 5 and 6).

The head 16 is introduced into the bore 18 of the bushing 17 such that its through-bore 25 is positioned in line with and as a continuation of those 22 of said bushing 17.

When the head 16 has an outer profile complementing the inner profile of the bore 18 of the bushing 17, said head can be fitted only in one position, leading automatically to the alignment of the bores 25 of the head 16 and that 22 of the bushing 17.

Figure 6:
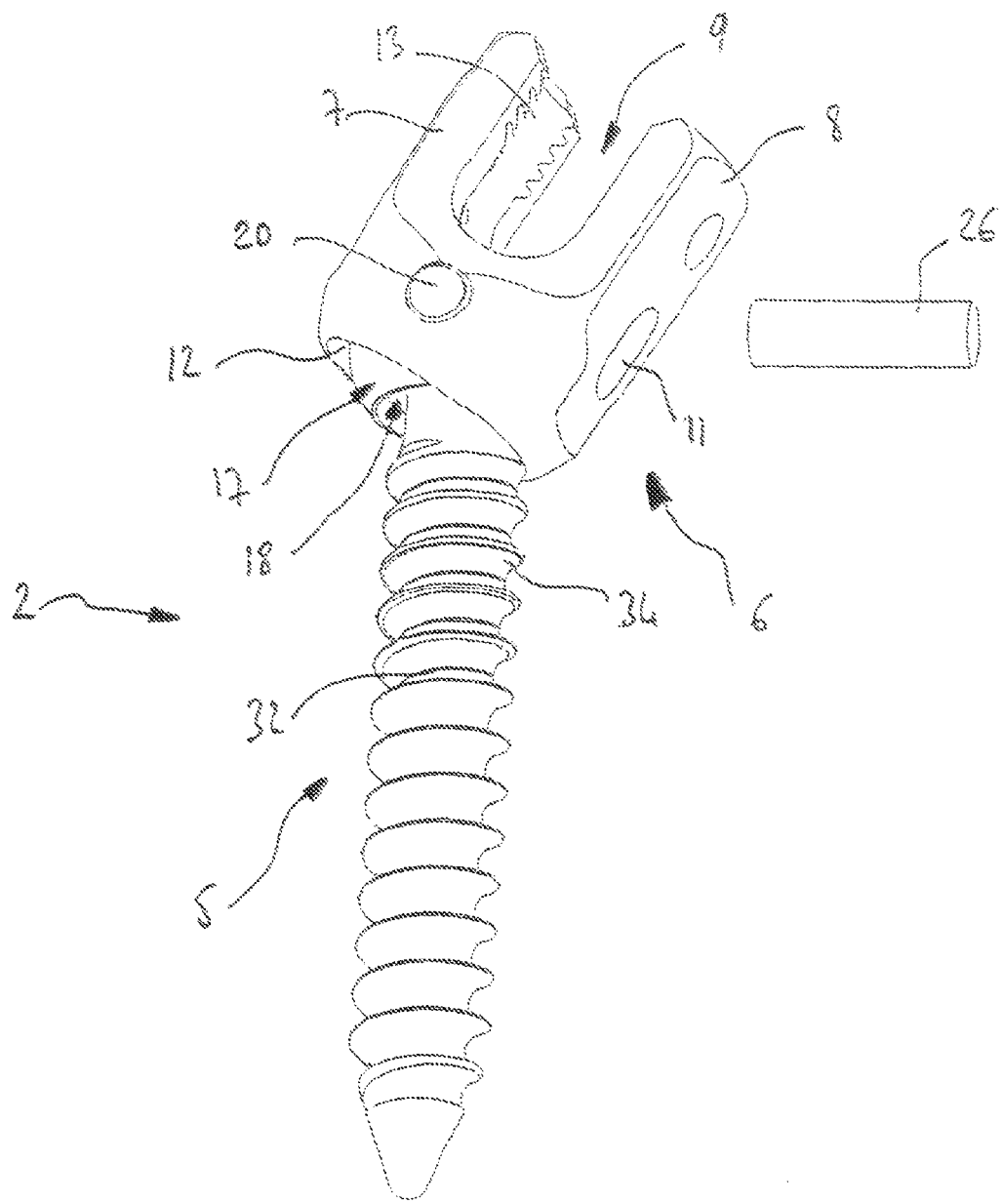

The connection element 6 is then inclined laterally about the rotation pins 20, 21, while maintaining the cylindrical body 33 of the anchoring screw 5 and the bushing 17 in a vertical position (FIG. 6).

This first lateral tilting movement makes it possible to position the first bore 22 of the bushing 17 and a first end of the bore 25 of the head 16 with one of the oblong openings 11 formed in the connection element 6.

This position permits introduction of the rotation pin 26, such that the latter passes through the corresponding oblong opening 11 of the connection element 6 and is positioned completely within the bores 22 of the bushing 17 and the bore 25 of the head 16 of the anchoring screw 5.

Figure 7:
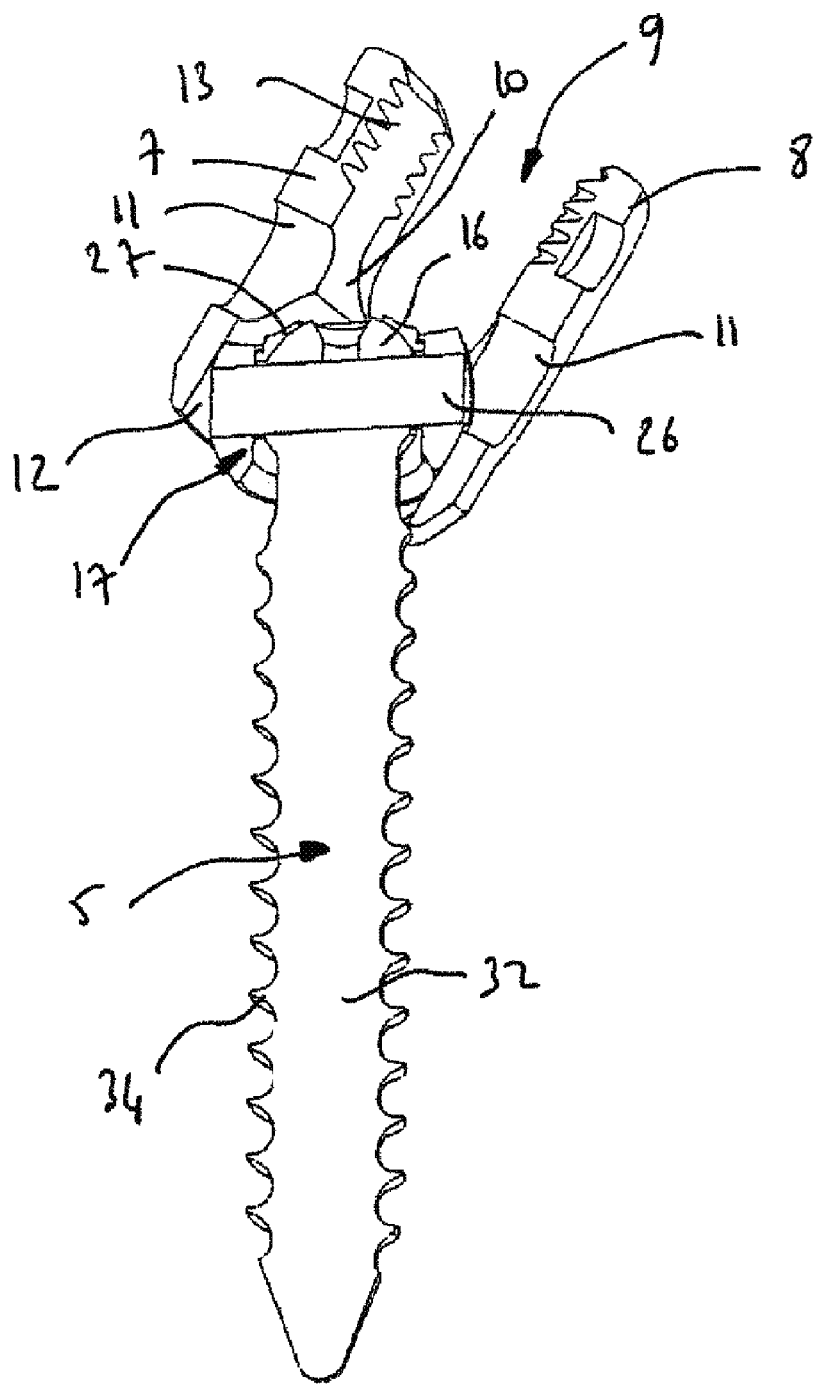

The fixation pin 26 is thus introduced completely inside the bores 22 of the bushing 17 and the bore 25 of the head 16 of the anchoring screw 5, making it possible to retain said anchoring screw 5 inside the bushing 17 (FIG. 7).

It will be noted that the dimensions of the fixation pin 26 are smaller than the external dimensions of the bushing 17, which means that once it has been introduced completely into the bores 22 of the bushing 17 and the bore 25 of the head 16 of the anchoring screw 5, the bushing 17 and the connection element 6 are able to tilt freely about the rotation pins 20, 21.

It will be observed that each connector 2 of the vertebral anchoring device 1 has:
a first lateral tilting movement about the rotation pins 20, 21 joining the bushing 17 to the connection element 6, and a second lateral tilting movement about the retention pin 26 joining the head 16 of the anchoring screw 5 to the bushing 17, the retention pin 26 being arranged in a direction that is horizontal and perpendicular to that of the horizontal rotation pins 20, 21.

It will be noted that the connection of the anchoring screw 5 to the bushing 17 and of the latter to the connection element 6 by way of the horizontal pins 20, 21 and 26 also ensures that the anchoring screw 5 is moved in rotation about its longitudinal axis in order for its cylindrical body 33 to penetrate into the corresponding vertebral body or vertebra 4.

The anchoring screw 5 is driven in rotation, so as to fix it in the corresponding vertebra 4, by means of a special tool (not shown) that cooperates with the connection element 6.

When the anchoring screw 5 of each connector 2 is fixed in the vertebral body 4, the connection element 6 is positioned in the best angular position by tilting about the horizontal pins 20, 21 and 26, so as to receive the connecting rod 3 that joins each connector 2 on the instrumented segment of the vertebral column.

Figure 9:
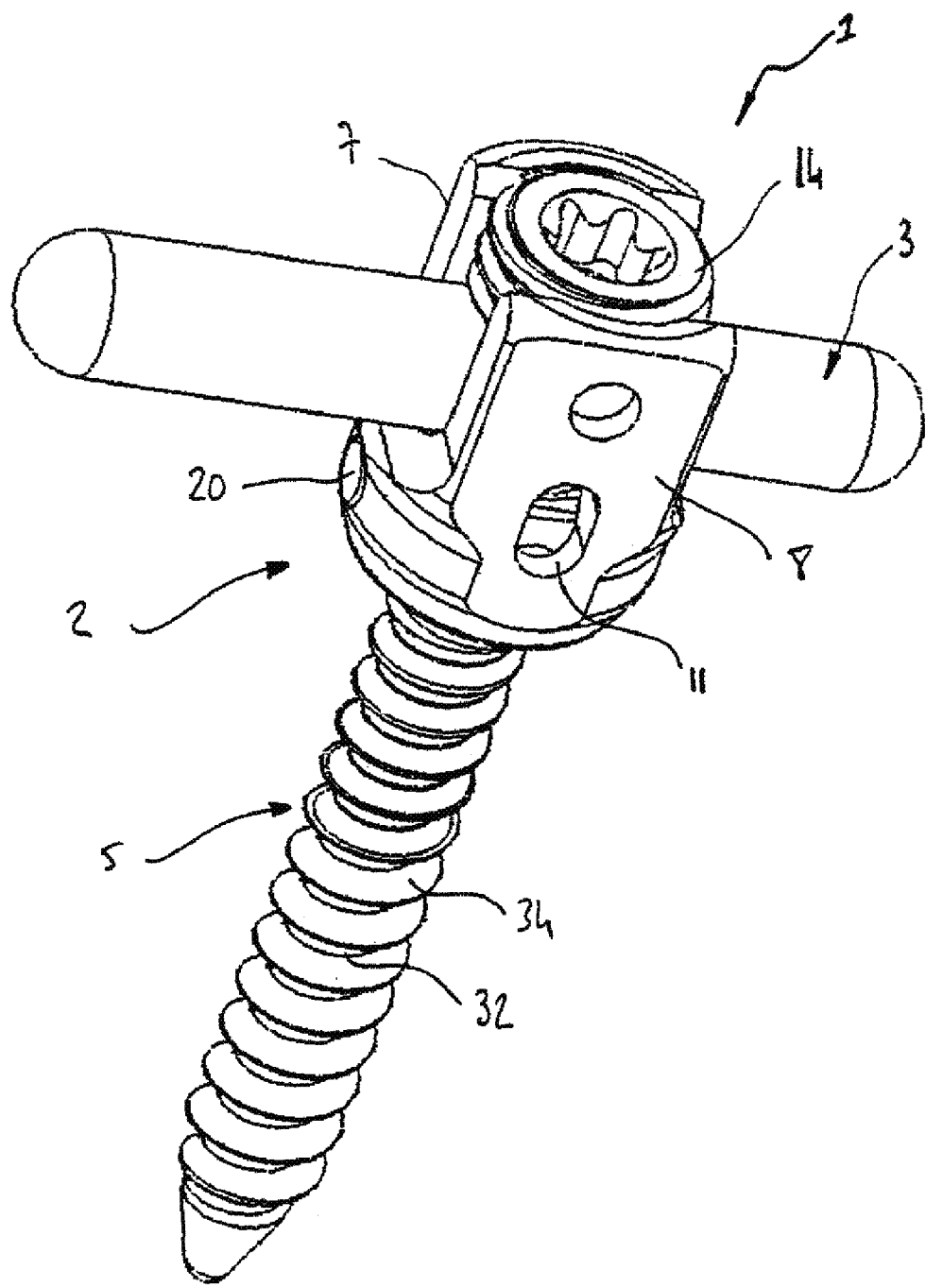
Figure 10:
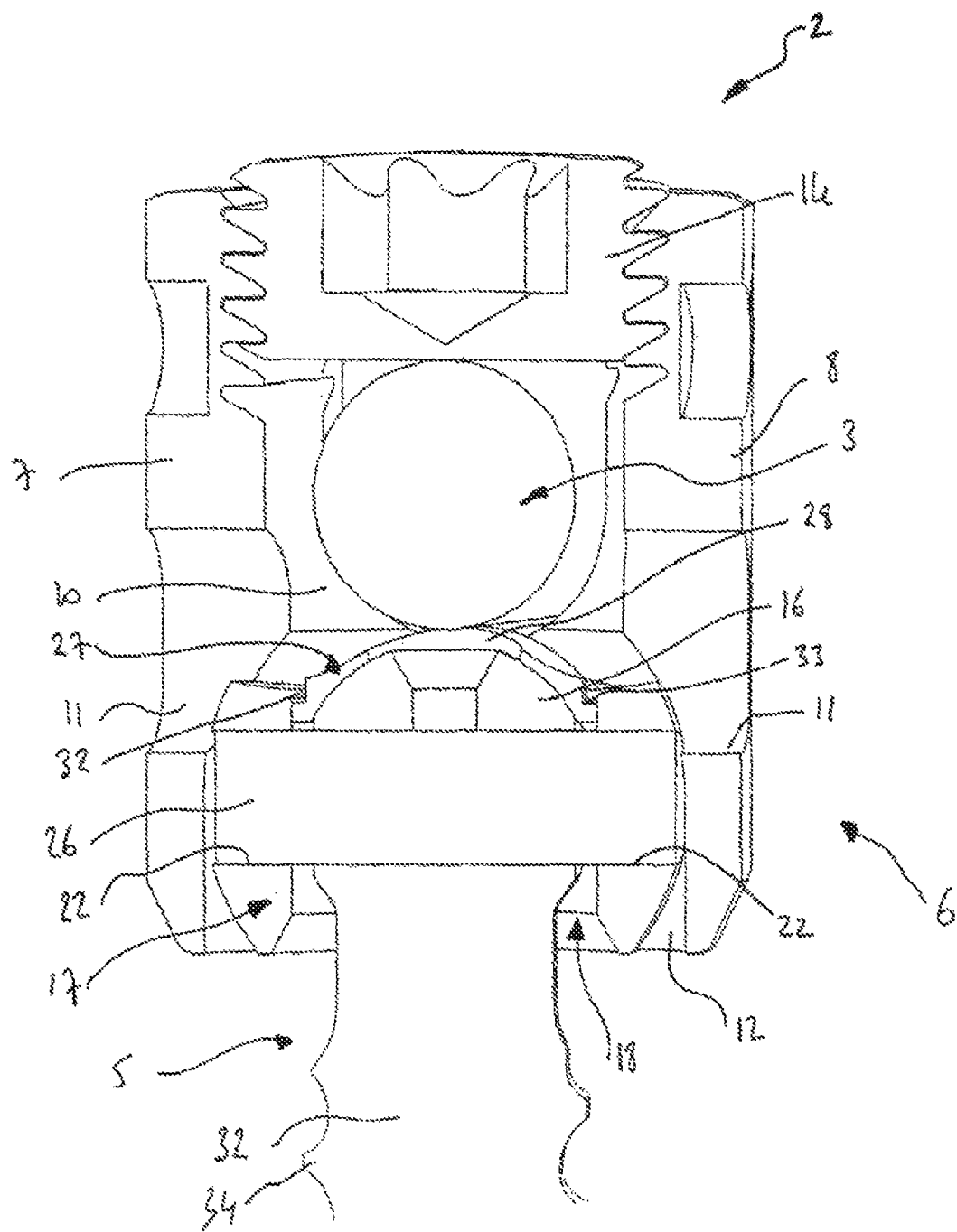

Inside each connector 2, the connecting rod 3 is immobilized, in terms of rotation about its longitudinal axis and in terms of translation, by the press-screw 14 that is screwed in between the upper vertical branches 7 and 8 of the connection element 6 (FIGS. 8 to 10).

The immobilization of the connecting rod 3 in the bottom of the opening 9 of each connection element 6 by the press-screw 14 also makes it possible to simultaneously block the connection element 6 in a suitable angular position about the head 16 of the anchoring screw 5.

This is because the ring 27, by way of its central bore 28, allows the head 16 of the anchoring screw 5 to take up a position at the bottom 10 of the opening 9 that receives the connecting rod 3.

The fixation of the connecting rod 3 between the vertical branches 7, 8 and against the bottom 10 of the opening 9 by means of the press-screw 14 allows the latter to bear against the head 16 of the anchoring screw 5 and block the connection element 6 (FIGS. 9 and 10).

It must be understood, moreover, that the above description has been given only by way of example and that it does not in any way limit the field of the invention, and that replacing the described details by other equivalent ones would not constitute a departure from said field of the invention.

The invention claimed is:

1. A vertebral anchoring device comprising:
a connecting rod (3);
bone-anchoring screws (5) implantable in the vertebrae (4) of a vertebral column, the bone-anchoring screws each comprising a head (16); and
connectors (2) linked to one another by the connecting rod (3) and fixed on the bone-anchoring screws (5),
each connector (2) being composed of a connection element (6) that comprises receiving and fixing parts to permit immobilization of the connecting rod (3) in translation and in rotation,
each connection element (6) further comprising, opposite the receiving and fixing parts, a seat (12) that cooperates with a connecting device (17) permitting assembly of the bone-anchoring screw (5),
the connecting device (17), before immobilization of the connecting rod (3) in the connection element (6), permitting, i) lateral and independent tilting movements of the connection element (6) and of the bone-anchoring screw (5) relative to each other and, ii) rotation of the bone-anchoring screw (5) for fixing the bone-anchoring screw (5) in the body of the vertebra (4), wherein,
the connecting device is composed of a bushing (17) that cooperates with the seat (12) of the connection element (6) and has first set of through-bores (15, 19) which are formed respectively in the seat (12) and the bushing (17) and allow the bushing to tilt laterally about rotation pins (20, 21), and second set of through-bores (22, 25) which are formed respectively in the bushing (17) and the head (16) of the bone-anchoring screw (5) and allow the bone-anchoring screw (5) to tilt laterally about another rotation pin (26).

2. The vertebral anchoring device according to claim 1, wherein the bushing (17) has at a center thereof, and extending in a vertical direction, an inner through-bore (18) designed to receive the head (16) of the bone-anchoring screw (5).

3. The vertebral anchoring device according to claim 2, wherein,
the first set of through-bores (15, 19) comprises i) first pair of through-bores (15) formed in the seat (12) of the connection element (6), and ii) a second pair of through-bores (19) extending in a first horizontal direction through the bushing (17), and
the first pair of through-bores (19) opens into the inner through-bore (18) of the bushing (17) and permits placement of the rotation pins (20, 21), such that the rotation pins (20, 21) extend into the first pair of through-bores (15) formed in the seat (12) of the connection element (6), so as to permit the first lateral tilting movement.

4. The vertebral anchoring device according to claim 3, wherein,
the receiving and fixing parts of each connection element (6) comprises upper vertical branches (7, 8) that i) delimit a U-shaped opening (9) for receiving said connecting rod, and, ii) above a bottom (10) of the U-shaped opening (9), comprise a threaded section (13) that allows a press-screw (14) to be tightened in order to block the connecting rod (3) in translation and in rotation, the connection element (6) further comprises, below the threaded section (13) and at a base of each vertical branch (7, 8), an oblong opening (11) that opens into an inside of said connection element, in an area of communication between the bottom (10) of the U-shaped opening (9) and the seat (12), in a horizontal direction perpendicular to a direction of the connecting rod (3), and the first pair of through-bores (15) of the seat (12) of the connection element (6) are arranged in a direction that is horizontal and perpendicular to a direction of the oblong opening (11) of each vertical branch (7, 8).

5. The vertebral anchoring device according to claim 2, wherein, the second set of through-bores (22, 25) comprises i) a third set of through-bores (22) extending through the bushing (17) in a second horizontal direction perpendicular to the first horizontal direction, and ii) a through-bore (25) formed in the head (16) of the bone-anchoring screw (5), and the third set of through-bores (22) open into the inner through-bore (18) of the bushing (17) and permits placement of the another rotation pin (26) that passes through through-bore (25) formed in the head (16) of the anchoring screw (5), so as to permit the second lateral tilting movement.

6. The vertebral anchoring device according to claim 5, wherein, the receiving and fixing parts of each connection element (6) comprises upper vertical branches (7, 8) delimiting a U-shaped opening (9) for receiving said connecting rod (3), said upper vertical branches (7, 8) comprising, above a bottom (10) of the U-shaped opening (9), a threaded section (13) that allows a press-screw (14) to be tightened in order to block the connecting rod (3) in translation and in rotation, the connection element (6) further comprises, below the threaded section (13) and at a base of each vertical branch (7, 8), an oblong opening (11) that opens into an inside of said connection element, in an area of communication between the bottom (10) of the U-shaped opening (9) and the seat (12), in a horizontal direction perpendicular to a direction of the connecting rod (3), and the first pair of through-bores (15) of the seat (12) of the connection element (6) are arranged in a direction that is horizontal and perpendicular to a direction of the oblong opening (11) of each vertical branch (7, 8).

7. The vertebral anchoring device according to claim 2, wherein, the first set of through-bores (15, 19) comprises i) first pair of through-bores (15) formed in the seat (12) of the connection element (6), and ii) a second pair of through-bores (19) extending in a first horizontal direction through the bushing (17), the second set of through-bores (22, 25) comprises i) a third set of through-bores (22) extending through the bushing (17) in a second horizontal direction perpendicular to the first horizontal direction, and ii) a through-bore (25) formed in the head (16) of the bone-anchoring screw (5), and the bushing (17) comprises an upper peripheral edge (23) which has, i) a hump (24) arranged above each through-bore (19) of the second pair of through-bores (19) and, ii) ribs (32) arranged above each through-bore (22) of the third set of through-bores (22) and inside the inner through-bore (18) of the bushing (17).

8. The vertebral anchoring device according to claim 7, wherein the bushing (17) is joined to a ring (27) which, at a center of the ring (27), has a hole (28) extending in a vertical direction, and, on an outer circumference of the ring (27), has recesses (30) cooperating with the ribs (32) of said bushing (17).

9. The vertebral anchoring device according to claim 1, wherein, the receiving and fixing parts of each connection element (6) comprises upper vertical branches (7, 8) that delimit a U-shaped opening (9) for receiving said connecting rod, said upper vertical branches (7, 8) comprising, above a bottom (10) of the U-shaped opening (9), a threaded section (13) that allows a press-screw (14) to be tightened in order to block the connecting rod (3) in translation and in rotation.

10. The vertebral anchoring device according to claim 9, wherein, the connection element (6) comprises, below the threaded section (13) and at a base of each vertical branch (7, 8), an opening (11) that opens into an inside of said connection element, in an area of communication between the bottom (10) of the U-shaped opening (9) and the seat (12), in a horizontal direction perpendicular to a direction of the connecting rod (3).

11. The vertebral anchoring device according to claim 10, wherein each of the openings (11), that open into the inside of said connection element, are arranged opposite each other and has an oblong vertical profile.

* * * * *